US011925907B2

United States Patent
Adair et al.

(10) Patent No.: US 11,925,907 B2
(45) Date of Patent: Mar. 12, 2024

(54) CONTINUOUS CRYSTALLIZATION OF CANNABINOIDS IN A STIRRED-TANK REACTOR

(71) Applicant: Canopy Growth Corporation, Smiths Falls (CA)

(72) Inventors: Christopher Adair, Smiths Falls (CA); Ben Geiling, Smiths Falls (CA)

(73) Assignee: Canopy Growth Corporation, Smiths Falls (CA)

( * ) Notice: Subject to any disclaimer, the term of this patent is extended or adjusted under 35 U.S.C. 154(b) by 229 days.

(21) Appl. No.: 17/628,853

(22) PCT Filed: Jul. 21, 2020

(86) PCT No.: PCT/CA2020/051005
§ 371 (c)(1),
(2) Date: Jan. 20, 2022

(87) PCT Pub. No.: WO2021/012044
PCT Pub. Date: Jan. 28, 2021

(65) Prior Publication Data
US 2022/0249976 A1    Aug. 11, 2022

Related U.S. Application Data

(60) Provisional application No. 62/877,071, filed on Jul. 22, 2019.

(51) Int. Cl.
*B01J 19/18*    (2006.01)
*A61K 31/05*    (2006.01)
(Continued)

(52) U.S. Cl.
CPC ............ *B01D 9/0036* (2013.01); *A61K 31/05* (2013.01); *A61K 31/352* (2013.01);
(Continued)

(58) Field of Classification Search
CPC .. B01D 9/0036; B01D 9/0063; B01D 9/0009; B01D 9/0018; B01D 11/0203;
(Continued)

(56) References Cited

U.S. PATENT DOCUMENTS 7,244,307 B2    7/2007 McCausland
7,402,686 B2    7/2008 Duchek
(Continued)

FOREIGN PATENT DOCUMENTS

CA    3024431 A1    1/2019
CN    108083989 A    5/2018
(Continued)

OTHER PUBLICATIONS

Castillo-Peinado et al., "The role of ultrasound in pharmaceutical production: Sonocrystallization", *Journal of Pharmacy and Pharmacology*, 2016, 68(10): 1249-1267.
(Continued)

*Primary Examiner* — Robert M Kunemund
(74) *Attorney, Agent, or Firm* — Knobbe, Martens, Olson & Bear LLP (57) ABSTRACT

Disclosed herein is a method for continuously preparing crystalline cannabinoid particles. The method includes preparing a cannabinoid-rich solution that comprises a first cannabinoid and inducing the cannabinoid-rich solution to a supersaturated state in which the first cannabinoid has a supersaturated concentration that is greater than a corresponding saturation concentration of the first cannabinoid. The method includes flowing the cannabinoid-rich solution into a continuous stirred-tank reactor (CSTR) in a continuous manner, mixing the cannabinoid-rich solution under turbulent mixing conditions to form a plurality of crystalline cannabinoid particles and a cannabinoid-depleted solution within the CSTR, and discharging the plurality of crystalline
(Continued)

cannabinoid particles and the cannabinoid-depleted solution from the CSTR in a continuous manner to provide a flow rate through the CSTR. The method includes separating crystalline cannabinoid particles from the plurality of crystalline cannabinoid particles and the cannabinoid-depleted solution in a continuous manner.

19 Claims, 3 Drawing Sheets (51) Int. Cl.
  A61K 31/352     (2006.01)
  A61K 36/185     (2006.01)
  B01D 9/00       (2006.01)
  B01D 11/02      (2006.01)
  B01J 4/00       (2006.01)
  B01J 19/00      (2006.01)
  C07B 63/00      (2006.01)

(52) U.S. Cl.
  CPC .......... *A61K 36/185* (2013.01); *B01D 9/0063* (2013.01); *B01D 11/0203* (2013.01); *B01D 11/0288* (2013.01); *B01J 4/001* (2013.01); *B01J 19/0066* (2013.01); *B01J 19/18* (2013.01); *C07B 63/00* (2013.01); *B01D 9/0009* (2013.01); *B01D 9/0018* (2013.01); *C07B 2200/13* (2013.01)

(58) Field of Classification Search
  CPC .. B01D 11/0288; A61K 31/05; A61K 31/352; A61K 36/185; B01J 31/05; B01J 4/001; B01J 19/0066; B01J 19/18; C07B 2200/13; C07B 63/00; C30B 29/54
  See application file for complete search history.

(56) References Cited

U.S. PATENT DOCUMENTS

| 8,106,244 | B2 | 1/2012 | Burdick et al. |
| 8,846,409 | B2 | 9/2014 | Flockhart et al. |
| 9,162,160 | B2 | 10/2015 | Robinson et al. |
| 9,333,229 | B2 | 5/2016 | Bjorncrantz |
| 9,376,367 | B2 | 6/2016 | Herkenroth et al. |
| 9,469,548 | B2 | 10/2016 | Mancosky |
| 9,642,798 | B2 | 5/2017 | Lipp et al. |
| 9,682,332 | B2 | 6/2017 | Ni et al. |
| 9,683,777 | B2 | 6/2017 | Moorkanikkara |
| 9,765,000 | B2 | 9/2017 | Nadal Roura |
| 9,937,480 | B2 | 4/2018 | Hong et al. |
| 10,053,407 | B2 | 8/2018 | Dickman et al. |
| 10,189,762 | B1 * | 1/2019 | Oroskar .................. C07C 37/82 |
| 10,195,159 | B2 | 2/2019 | Whittle et al. |
| 10,207,199 | B2 | 2/2019 | Nadal Roura |
| 10,212,953 | B2 | 2/2019 | Ni et al. |
| 10,843,991 | B2 * | 11/2020 | Oroskar ............... A61K 31/352 |
| 2006/0167283 | A1 | 7/2006 | Flockhart et al. |
| 2012/0315308 | A1 | 12/2012 | Travers |
| 2014/0256980 | A1 | 9/2014 | Li |
| 2014/0328731 | A1 | 11/2014 | Ni et al. |
| 2016/0250615 | A1 | 9/2016 | Azevedo Ferreira et al. |
| 2017/0008870 | A1 | 1/2017 | Dibble et al. |
| 2017/0349518 | A1 | 12/2017 | Dickman et al. |
| 2018/0362429 | A1 | 12/2018 | Zhang et al. |
| 2019/0002449 | A1 | 1/2019 | De Keyser et al. |
| 2019/0010106 | A1 | 1/2019 | Oroskar et al. |
| 2019/0010110 | A1 | 1/2019 | Oroskar et al. |
| 2019/0134121 | A1 | 5/2019 | Bermudez et al. |
| 2019/0134532 | A1 | 5/2019 | Nadal Roura |

FOREIGN PATENT DOCUMENTS

| CN | 207384904 U | 5/2018 |
| CN | 108314608 A | 7/2018 |
| CN | 207591325 U | 7/2018 |
| CN | 109053388 A | 12/2018 |
| CN | 208292897 U | 12/2018 |
| EP | 1965900 B1 | 12/2014 |
| EP | 3274321 B1 | 9/2019 |
| WO | WO 2004/026452 A1 | 4/2004 |
| WO | WO 2013/043044 A1 | 3/2013 |
| WO | WO 2016/107968 A1 | 7/2016 |
| WO | WO 2016/116628 A1 | 7/2016 |
| WO | WO 2018/023087 A1 | 2/2018 |
| WO | WO 2018/113888 A1 | 6/2018 |
| WO | WO 2018/160827 A1 | 9/2018 |
| WO | WO 2019/005526 A1 | 1/2019 |
| WO | WO 2019/020738 A1 | 1/2019 |
| WO | WO 2019/056129 A2 | 3/2019 |
| WO | WO 2019/069312 A2 | 4/2019 |

OTHER PUBLICATIONS

Jordens et al., "Ultrasound Assisted Particle Size Control by Continuous Seed Generation and Batch Growth", *Crystals*, 2017, 7(7): 195.

Lawton et al., "Continuous Crystallization of Pharmaceuticals Using a Continuous Oscillatory Baffled Crystallizer", *Organic Process Research & Development*, 2009, 13(6): 1357-1363.

* cited by examiner

CONTINUOUS CRYSTALLIZATION OF CANNABINOIDS IN A STIRRED-TANK REACTOR

CROSS-REFERENCE TO RELATED APPLICATION

This application is a national stage filing under 35 U.S.C. 371 of International Application No. PCT/CA2020/051005, which is hereby incorporated by reference in its entirety, which claims priority to and benefit of U.S. Provisional Patent Application Ser. No. 62/877,071 filed on Jul. 22, 2019, which is hereby incorporated by reference.

TECHNICAL FIELD

The present disclosure generally relates to methods of crystallizing cannabinoids. In particular, the present disclosure relates to continuous-mode cannabinoid-crystallization methods as opposed to batch-mode cannabinoid-crystallization methods.

BACKGROUND

Cannabinoids are often defined in pharmacological terms as a class of compounds that exceed threshold-binding affinities for specific receptors found in central-nervous-system tissues and/or peripheral tissues. The interactions between cannabinoids and their receptors are under active investigation by a number of researchers, because the resultant effects are demonstrably important both in medicinal and reactional contexts. Many medicinal and recreational cannabinoid products feature cannabinoids in crystalline form. Methods for producing such products typically rely on batch-mode crystallization protocols. Unfortunately, batch-mode crystallization protocols are difficult to control—especially at large scale—and they are often associated with inconsistent product specifications (such as crystal-size distribution, polymorphic form, and/or crystal morphology). Such inconsistent product specifications may negatively impact downstream processes and/or consumer experiences in both medicinal and recreational contexts.

In recent years, continuous crystallization technologies have emerged as viable alternatives to batch-mode crystallization technologies. Continuous-crystallization methods are associated with efficient use of solvents, energy, and space, and they are associated with minimal waste production. Continuous stirred-tank reactors (CSTRs) are a type of reactor that can be configured to operate in a manner that is suitable for inducing crystallization in a continuous-mode process. Continuous-crystallization methods may be designed towards providing near plug-flow conditions (i.e. conditions under which a fluid flows with minimal shearing between adjacent layers) by operating multiple CSTRs in series.

CSTRs typically feature an impeller and baffles to provide turbulent agitation to fluid within the CSTR. Fluid turbulence in a CSTR is associated with continuous generation of swirling eddy currents due to fluid-impeller and/or fluid-baffle interactions. The fluid mechanics associated with such conditions are highly complex in that there are a number of confounding variables contributing to turbulent mixing conditions (e.g. impeller geometry, impeller speed, impeller location within the CSTR, baffle spacing, baffle geometry, baffle orientation, fluid viscosity, etc.). At the same time, there are number of confounding variables that impact the pre-crystallization behavior of a solution as it transitions from an undersaturated state to a supersaturated state. Likewise, there are a number of confounding variables that impact crystal nucleation and crystal growth. Accordingly, it is difficult to predict the particular physical-chemical parameters and mixing conditions that will navigate the metastable states required to induce continuous crystallization of a particular type of material from a particular solution. Researchers are often confounded when applying systematic approaches to continuously crystallizing target compounds from CSTRs, and this is particularly true for complex mixtures of structurally similar compounds (e.g. regioisomers, stereoisomers, etc.) such as those associated with cannabinoid extracts, resins, distillates, crude isolates, and the like. Accordingly, methods for crystallizing cannabinoids under continuous-flow conditions to provide particular crystal-size distributions, polymorphic forms, and/or crystal morphologies are desirable.

SUMMARY

In contrast to the batch-mode crystallization methods typically employed for cannabinoid crystallization, the methods of the present disclosure utilize continuous stirred-tank reactors (CSTRs) that are configured for continuous flow under carefully controlled conditions. By modulating the fluid-mechanical parameters of such reactors to exploit the particular solution-phase characteristics of cannabinoids and/or mixtures of cannabinoids, the methods of the present disclosure provide access to a plurality of crystalline cannabinoid materials. In particular, the methods of the present disclosure provide access to crystalline-cannabinoid materials with narrow size distributions, and/or narrow polymorphic distributions. Without being bound to any particular theory, the present disclosure posits that these features are engendered by the utilization of turbulent mixing conditions in a CSTR.

In select embodiments, the present disclosure relates to a method for producing crystalline cannabinoid particles in continuous mode, the method comprising: preparing a cannabinoid-rich solution that comprises a first cannabinoid; inducing the cannabinoid-rich solution to a supersaturated state in which the first cannabinoid has a supersaturated concentration that is greater than a corresponding saturation concentration of the first cannabinoid; flowing the cannabinoid-rich solution into a continuous stirred-tank reactor (CSTR) in a continuous manner; mixing the cannabinoid-rich solution under turbulent mixing conditions to form a plurality of crystalline cannabinoid particles and a cannabinoid-depleted solution within the CSTR; discharging the plurality of crystalline cannabinoid particles and the cannabinoid-depleted solution from the CSTR in a continuous manner to provide a flow rate through the CSTR; and separating crystalline cannabinoid particles from the plurality of crystalline cannabinoid particles and the cannabinoid-depleted solution in a continuous manner, wherein the turbulent mixing conditions are defined by a Reynolds number that is greater than a critical Reynolds number for the cannabinoid-rich solution and the CSTR.

In select embodiments of the present disclosure, the critical Reynolds is about equal to a Reynolds number above which a power number for the reactor is about constant. In select embodiments of the present disclosure, the critical Reynolds number is greater than 10,000.

In select embodiments of the present disclosure, the CSTR has a capacity between about 30 cc and about 400 L.

In select embodiments of the present disclosure, mixing the cannabinoid-rich solution under turbulent mixing conditions includes mixing the cannabinoid-rich solution with a Rushton turbine, a propeller, an anchor impeller, a gate-anchor impeller, a paddle impeller, a helical-screw impeller, a helical-ribbon impeller, or a combination thereof.

In select embodiments of the present disclosure, the CSTR comprises a baffle that is shaped, oriented, or positioned to redirect flow within the CSTR. In select embodiments of the present disclosure, the baffle is one of a plurality of baffles.

In select embodiments of the present disclosure, the CSTR is cylindrical, the impeller is positioned and oriented to align the axis of rotation of the impeller with the cylinder axis. In select embodiments of the present disclosure, turbulently mixing the cannabinoid-rich solution with the mixer comprises turbulently mixing the cannabinoid-rich solution with the mixer wherein the impeller diameter is about one-third the diameter of the CSTR.

In select embodiments, the methods of the present disclosure further comprise cooling the cannabinoid-rich solution, the cannabinoid-depleted solution, or a combination thereof within the CSTR.

In select embodiments of the present disclosure, the first cannabinoid is THC (Δ9-THC), THCA, Δ8-THC, trans-Δ10-THC, cis Δ10-THC, THCV, THCVA, Δ8-THCV, Δ9-THCV, CBD, CBDA, CBDV, CBDVA, CBC, CBCA, CBCV, CBCVA, CBG, CBGA, CBGV, CBGVA, CBN, CBNA, CBNV, CBNVA, CBND, CBNDA, CBNDV, CBNDVA, CBE, CBEA, CBEV, CBEVA CBL, CBLA, CBLV, CBLVA, CBT, CBTA, or cannabicitran.

In select embodiments of the present disclosure, the cannabinoid-rich solution comprises a cannabinoid extract, a cannabinoid resin, a cannabinoid distillate, a cannabinoid isolate, or a combination thereof.

In select embodiments of the present disclosure, the cannabinoid-rich solution comprises THC (Δ9-THC), THCA, Δ8-THC, trans-Δ10-THC, cis Δ10-THC, THCV, THCVA, Δ8-THCV, Δ9-THCV, CBD, CBDA, CBDV, CBDVA, CBC, CBCA, CBCV, CBCVA, CBG, CBGA, CBGV, CBGVA, CBN, CBNA, CBNV, CBNVA, CBND, CBNDA, CBNDV, CBNDVA, CBE, CBEA, CBEV, CBEVA CBL, CBLA, CBLV, CBLVA, CBT, CBTA, cannabicitran, or a combination thereof.

In select embodiments of the present disclosure, the cannabinoid-rich solution comprises a solvent. The solvent may comprise pentane, hexane, heptane, methanol, ethanol, isopropanol, dimethyl sulfoxide, acetone, ethyl acetate, diethyl ether, tert-butyl methyl ether, water, acetic acid, anisole, 1-butanol, 2-butanol, butane, butyl acetate, ethyl formate, formic acid, isobutyl acetate, isopropyl acetate, methyl acetate, 3-methyl-1-butanol, methylethyl ketone, 2-methyl-1-propanol, 1-pentanol, 1-propanol, propane, propyl acetate, trimethylamine, or a combination thereof.

In select embodiments of the present disclosure, the cannabinoid-rich solution has a viscosity of between about 0.05 cP and about 250 cP at an inlet to the CSTR.

In select embodiments of the present disclosure, the cannabinoid-rich solution has a fluid density of between about 0.2 g/mL and about 1,700 g/mL at an inlet to the CSTR.

In select embodiments of the present disclosure, the cannabinoid-rich solution has a temperature of between about 0° C. and about 50° C. at an inlet to the CSTR.

In select embodiments of the present disclosure, the inducing of the cannabinoid-rich solution to the supersaturated state precedes the flowing of the cannabinoid-rich solution through the CSTR.

In select embodiments of the present disclosure, the inducing of the cannabinoid-rich solution to the supersaturated state is concurrent the mixing of the cannabinoid-rich solution.

In select embodiments of the present disclosure, the cannabinoid-rich solution further comprises an excipient.

In select embodiments, the methods of the present disclosure further comprise dispersing a plurality of seed crystals into the cannabinoid-rich solution concurrent with the mixing of the cannabinoid-rich solution.

In select embodiments, the methods of the present disclosure further comprise flowing the plurality of crystalline cannabinoid particles and the cannabinoid-depleted solution into an additional CSTR, mixing the plurality of crystalline cannabinoid particles and the cannabinoid-depleted solution to form a plurality of larger crystalline cannabinoid particles within the additional CSTR, and discharging the plurality of larger crystalline cannabinoid particles and the cannabinoid-depleted solution from the additional CSTR in a continuous manner to provide a flow rate through the CSTR. Separating crystalline cannabinoid particles from the plurality of crystalline cannabinoid particles and the cannabinoid-depleted solution may include separating the larger crystalline cannabinoid particles from plurality of crystalline cannabinoid particles and/or the cannabinoid-depleted solution.

In select embodiments of the present disclosure, mixing the cannabinoid-rich solution under turbulent mixing conditions includes mixing the cannabinoid-rich solution with an energy dissipation rate to produce eddies with a Kolmogorov length scale larger than the size of the crystalline cannabinoid particles.

In select embodiments of the present disclosure, inducing the cannabinoid-rich solution to a supersaturated state includes evaporating at least a portion of the cannabinoid-rich solution.

BRIEF DESCRIPTION OF THE DRAWINGS

These and other features of the present disclosure will become more apparent in the following detailed description in which reference is made to the appended drawings. The appended drawings illustrate one or more embodiments of the present disclosure by way of example only and are not to be construed as limiting the scope of the present disclosure.

DETAILED DESCRIPTION

Careful analysis of the solution-phase behavior of a range of cannabinoid solutions indicates that: (i) undersaturated cannabinoid solutions can be induced to supersaturate with strategic manipulation of temperature, pressure, solute, solvent, co-solvent, and/or non-solvent parameters; and (ii) turbulent flow conditions can be used to induce cannabinoid crystallization from supersaturated cannabinoid solution under controlled, repeatable conditions. In the context of the present disclosure the terms "supersaturate" and "supersaturation" refer to a meta-stable state in which a solution comprises a kinetically unstable quantity of solute such that spontaneous nucleation and/or induced nucleation is likely to occur. The methods of the present disclosure leverage the combination of such kinetically unstable solutions with turbulent mixing conditions to induce crystal nucleation and/or growth under controlled, repeatable conditions. The result is a series of methods that provide crystalline cannabinoid materials with narrow crystal-size distributions and consistent polymorphic character. Such crystalline cannabinoids are likely to be useful in both medical and recreational contexts.

In select embodiments, the present disclosure relates to a method for producing crystalline cannabinoid particles in continuous mode, the method comprising: preparing a cannabinoid-rich solution that comprises a first cannabinoid; inducing the cannabinoid-rich solution to a supersaturated state in which the first cannabinoid has a supersaturated concentration that is greater than a corresponding saturation concentration of the first cannabinoid; flowing the cannabinoid-rich solution into a continuous stirred-tank reactor (CSTR) in a continuous manner; mixing the cannabinoid-rich solution under turbulent mixing conditions to form a plurality of crystalline cannabinoid particles and a cannabinoid-depleted solution within the CSTR; discharging the plurality of crystalline cannabinoid particles and the cannabinoid-depleted solution from the CSTR in a continuous manner to provide a flow rate through the CSTR; and separating crystalline cannabinoid particles from the plurality of crystalline cannabinoid particles, the cannabinoid-depleted solution, or a combination thereof in a continuous manner, wherein the turbulent mixing conditions are defined by a Reynolds number that is greater than a critical Reynolds number for the cannabinoid-rich solution and the CSTR.

As will be appreciated by those skilled in the art who have benefitted from the teachings of the present disclosure, inducing a cannabinoid-rich solution into a supersaturated state primes the solution for cannabinoid crystallization. Such inducing may be driven by a variety of factors such as temperature decrease, pH adjustment, solute addition, solvent evaporation, co-solvent addition, non-solvent addition, or a combination thereof. Those skilled in the art who have benefitted from the teachings of the present disclosure will appreciate that the particulars of any such strategy for inducing a cannabinoid-rich solution into a supersaturated state will vary, but that the general concepts are similar such that the following discussion of temperature-driven supersaturation may be extrapolated to alternate approaches. With respect to temperature-driven supersaturation of a cannabinoid-rich solution, the particular cannabinoid-rich solution may be characterized by a saturation curve (i.e. a plot of saturation concentration as a function of temperature for a particular pressure) which delineates a boundary between undersaturation and supersaturation conditions. When a hot and undersaturated cannabinoid-rich solution is cooled, it approaches the corresponding point on the saturation curve (i.e. its saturation point). With further cooling, the cannabinoid-rich solution becomes supersaturated, such that the supersaturated solution is in a metastable state, wherein a suitable initiation event will induce nucleation and crystal growth. Nucleation and crystal growth decrease the concentration of the particular cannabinoid (i.e. desupersaturation), and the cannabinoid-rich solution is depleted towards the corresponding point on the saturation curve. While the solubility of the particular cannabinoid in solution may be readily determined experimentally, the supersolubility or the metastable limit for the cannabinoid-rich solution is difficult to define, because it depends on numerous factors such as the rate of supersaturation generation (i.e. cooling rate). Cannabinoid solubility studies indicate that inducing the cannabinoid-rich solution to a supersaturated state in which the particular cannabinoid has a supersaturated concentration that is greater than its corresponding saturation concentration provides sufficient supersaturation for turbulent-flow-induced nucleation and/or growth in a continuous fashion provided the turbulent-flow-related parameters meet particular conditions.

As will be appreciated by those skilled in the art who have benefited from the teachings of the present disclosure, turbulent mixing conditions within a CSTR may be quantified by the Reynolds number (Re) as defined as by EQN. 1.

$$Re_o = \frac{N_i D_i^2 \rho}{\mu} \qquad \text{EQN. 1}$$

Wherein:
$N_i$ is the rotation rate of the CSTR impeller (in $s^{-1}$);
$D_i$ is the diameter of the CSTR impeller (in m);
$\rho$ is the fluid density (in $kg/m^3$); and
$\mu$ is the fluid viscosity (kg/m·s).

The Reynolds number describes the intensity of mixing within a CSTR equipped with a single impeller. Those skilled in the art who have benefited from the teachings of the present disclosure will readily ascertain the related Reynolds number equations for alternate types of CSTRs. The severity of the turbulent flow conditions required to induce crystal nucleation/growth from a particular cannabinoid-rich solution will vary depending on the particulars of the cannabinoid rich solution and the extent of supersaturation. However, for any particular solution/CSTR combination, there is a critical Reynolds number that defines the minimum conditions required to ensure turbulent mixing.

As will be appreciated by those skilled in the art who have benefited from the teachings of the present disclosure, turbulent mixing conditions within a CSTR may be further quantified by the Power Number ($N_p$) as defined as by EQN. 2.

$$N_P = \frac{P}{\rho N_i^3 D_i^5} \qquad \text{EQN. 2}$$

Wherein:
P is the input power (in $kg \cdot m^2/s^{-3}$)
$\rho$ is the fluid density (in $kg/m^3$);
$N_i$ is the rotation rate of the CSTR impeller (in $s^{-1}$); and
$D_i$ is the diameter of the CSTR impeller (in m).

The power number describes the relationship between the power applied to the impeller in a CSTR and the force exerted by the fluid in the CSTR resisting the movement of the impeller. The power number for a CSTR filled with a particular fluid may be compared to the Reynolds number for said CSTR, for example with a plot of power number as a function of Reynolds number. For relatively low values for the Reynolds number (i.e. for Reynolds numbers corresponding to laminar mixing conditions), the power number decreases as Reynolds number increases. For relatively high values for the Reynolds number (i.e. for Reynolds numbers corresponding to turbulent mixing conditions), the power number remains about constant as the Reynolds number increases. Accordingly, without being bound to any particular theory, the present disclosure posits that a cannabinoid solution within a CSTRs may be characterized by a minimum Reynolds number above which the power number remains about constant. In other words, said minimum Reynolds number defines conditions that may ensure turbulent mixing.

In the context of the present disclosure, the terms "crystal", "crystallizing", "crystalline", and the like are used broadly to refer to a spectrum of solid materials having a degree of microscopic order but not necessarily a highly ordered crystal lattice that extends in all directions. As will be appreciated by those skilled in the art who have benefitted from the teachings of the present disclosure, the degree of crystallinity of material can be evaluated by a variety of means such as but not limited to powder X-ray diffraction, single-crystal X-ray diffraction, differential scanning calorimetry, and the like.

The cannabinoid-rich solution may be prepared from a distillate, a resin, an extract, or the like. For example, the cannabinoid-rich solution may be prepared by solvent extraction from marijuana or hemp. The extraction solvent may be supercritical carbon dioxide, ethanol, heptane, pentane, propane, n-butane, iso-butane, or any Class 3 solvent as defined by the International Conference on Harmonization (ICH) guidelines. Optionally, the solvent extract (or the cannabinoid-rich solution more generally) may be further refined using purification processes including but not limited to filtration, winterization (i.e. precipitation of undesired plant waxes using organic solvent at or below ambient temperature), distillation, chromatography (e.g. normal-phase, reversed-phase, centrifugal partition, simulated moving bed), trituration, liquid-liquid extraction, and solid-liquid extraction. The cannabinoids in the cannabinoid-rich solution may also be of synthetic origin.

The cannabinoids of the cannabinoid-rich solution may also be combined with an excipient(s) (e.g. basic molecules, acidic molecules, co-formers, derivatization agents) prior to crystallization to modify the physical and/or chemical properties of the cannabinoids and/or the cannabinoid-rich solution. For example, cannabinoids may be incubated with a basic molecule, such as an alkaloid or basic amino acid, to form the carboxylate salt of the cannabinoid of interest. This modification may serve to improve the crystallization process and/or to modify the physical/chemical properties of the cannabinoid of interest. Cannabinoids of the cannabinoid-rich solution may also be combined with acidic molecules and/or co-formers prior to crystallization to form a co-crystal with the cannabinoid of interest during the crystallization process. This modification may serve to improve the crystallization process and/or to modify the physical/chemical properties of the cannabinoid of interest.

Cannabinoids of the cannabinoid-rich solution may also be combined with derivatization agents prior to crystallization to form a chemical derivative of the cannabinoid of interest. This modification may serve to improve the crystallization process and/or to modify the physical/chemical properties of the cannabinoid of interest. For example, tetrahydrocannabinol (THC) is an oil under ambient conditions and does not readily crystallize. Functionalization of the phenolic hydroxyl group of THC with certain ester or sulfonic ester moieties may enable crystallization of otherwise non-crystallisable cannabinoids including but not limited to $\Delta^9$-tetrahydrocannabinol, $\Delta^8$-tetrahydrocannabinol, and/or cannabinol. Alternatively, esters of acidic cannabinoids made by synthetic means can be used as the cannabinoids in the cannabinoid cannabinoid-rich solution.

As used herein, the term "cannabinoid" refers to: (i) a chemical compound belonging to a class of secondary compounds commonly found in plants of genus *Cannabis*, (ii) synthetic cannabinoids and any enantiomers thereof; and/or (iii) one of a class of diverse chemical compounds that may act on cannabinoid receptors such as CB1 and CB2.

In select embodiments of the present disclosure, the cannabinoid is a compound found in a plant, e.g., a plant of genus *Cannabis*, and is sometimes referred to as a phyto-cannabinoid. One of the most notable cannabinoids of the phytocannabinoids is tetrahydrocannabinol (THC), the primary psychoactive compound in *Cannabis*. Cannabidiol (CBD) is another cannabinoid that is a major constituent of the phytocannabinoids. There are at least 113 different cannabinoids isolated from *Cannabis*, exhibiting varied effects.

In select embodiments of the present disclosure, the cannabinoid is a compound found in a mammal, sometimes called an endocannabinoid.

In select embodiments of the present disclosure, the cannabinoid is made in a laboratory setting, sometimes called a synthetic cannabinoid. In one embodiment, the cannabinoid is derived or obtained from a natural source (e.g. plant) but is subsequently modified or derivatized in one or more different ways in a laboratory setting, sometimes called a semi-synthetic cannabinoid.

In many cases, a cannabinoid can be identified because its chemical name will include the text string "*cannabi*". However, there are a number of cannabinoids that do not use this nomenclature, such as for example those described herein.

As well, any and all isomeric, enantiomeric, or optically active derivatives are also encompassed. In particular, where appropriate, reference to a particular cannabinoid includes both the "A Form" and the "B Form". For example, it is known that THCA has two isomers, THCA-A in which the carboxylic acid group is in the 1 position between the hydroxyl group and the carbon chain (A Form) and THCA-B in which the carboxylic acid group is in the 3 position following the carbon chain (B Form). As will be appreciated by those skilled in the art who have benefitted from the teachings of the present disclosure, the terms "first cannabinoid" may refer to: (ii) salts of acid forms, such as $Na^+$ or $Ca^{2+}$ salts of such acid forms; and/or (iii) ester forms, such as formed by hydroxyl-group esterification to form traditional esters, sulphonate esters, and/or phosphate esters.

Examples of cannabinoids include, but are not limited to, Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Δ6-Cannabidiol (Δ6-CBD), Cannabidiol monomethylether (CBDM), Cannabidiol-C4 (CBD-C4), Cannabidivarinic Acid (CBDVA), Cannabidivarin (CBDV), Cannabidiorcol (CBD-C1), Tetrahydrocannabinolic acid A (THCA-A), Tetrahydrocannabinolic acid B (THCA-B), Tetrahydrocannabinol (THC or Δ9-THC), Δ8-tetrahydrocannabinol (Δ8-THC), trans-Δ10-tetrahydrocannabinol (trans-Δ10-THC), cis-Δ10-tetrahydrocannabinol (cis-Δ10-THC), Tetrahydrocannabinolic acid C4 (THCA-C4), Tetrahydrocannabinol C4 (THC-C4), Tetrahydrocannabivarinic acid (THCVA), Tetrahydrocannabivarin (THCV), Δ8-Tetrahydrocannabivarin (Δ8-THCV), Δ9-Tetrahydrocannabivarin (Δ9-THCV), Tetrahydrocannabiorcolic acid (THCA-C1), Tetrahydrocan- nabiorcol (THC-C1), Δ7-cis-iso-tetrahydrocannabivarin, Δ8-tetrahydrocannabinolic acid (Δ8-THCA), Δ9-tetrahydrocannabinolic acid (Δ9-THCA), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabinolic acid (CBNA), Cannabinol (CBN), Cannabinol methylether (CBNM), Cannabinol-C4 (CBN-C4), Cannabivarin (CBV), Cannabino-C2 (CBN-C2), Cannabiorcol (CBN-C1), Cannabinodiol (CBND), Cannabinodivarin (CBDV), Cannabitriol (CBT), 11-hydroxy-Δ9-tetrahydrocannabinol (11-OH-THC), 11 nor 9-carboxy-Δ9-tetrahydrocannabinol, Ethoxy-cannabitriolvarin (CBTVE), 10-Ethoxy-9-hydroxy-Δ6a-tetrahydrocannabinol, Cannabitriolvarin (CBTV), 8,9 Dihydroxy-Δ6a(10a)-tetrahydrocannabinol (8,9-Di-OH-CBT-C5), Dehydrocannabifuran (DCBF), Cannbifuran (CBF), Cannabichromanon (CBCN), Cannabicitran, 10-Oxo-Δ6a(10a)-tetrahydrocannabinol (OTHC), Δ9-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Epigallocatechin gallate, Dodeca-2E, 4E, 8Z, 10Z-tetraenoic acid isobutylamide, hexahydrocannibinol, and Dodeca-2E,4E-dienoic acid isobutylamide.

Within the context of this disclosure, where reference is made to a particular cannabinoid without specifying if it is acidic or neutral, each of the acid and/or decarboxylated forms are contemplated as both single molecules and mixtures.

As used herein, the term "THC" refers to tetrahydrocannabinol. "THC" is used interchangeably herein with "Δ9-THC".

In select embodiments of the present disclosure, the first cannabinoid may comprise THC (Δ9-THC), THCA, Δ8-THC, trans-Δ10-THC, cis-Δ10-THC, THCV, THCVA, Δ8-THCV, Δ9-THCV, CBD, CBDA, CBDV, CBDVA, CBC, CBCA, CBCV, CBCVA, CBG, CBGA, CBGV, CBGVA, CBN, CBNA, CBNV, CBNVA, CBND, CBNDA, CBNDV, CBNDVA, CBE, CBEA, CBEV, CBEVA, CBL, CBLA, CBLV, CBLVA CBT, CBTA, or cannabicitran.

Structural formulae of cannabinoids of the present disclosure may include the following:

THC

THCA

THCV

THCVA

Δ8-THC

Δ8-THCV

CBD

CBDA

-continued

CBNDA

CBNDV

CBNDVA

CBL

CBLA

CBLV

CBLVA

-continued

CBE

CBEA

CBEV

CBEVA trans-Δ10-THC cis-Δ10-THC

CBT
(cannabitriol)

cannabicitran

In select embodiments of the present disclosure, the first cannabinoid may comprise CBD, CBDV, CBC, CBCV, CBG, CBGV, THC, THCV, or a regioisomer thereof. As used herein, the term "regioisomers" refers to compounds that differ only in the location of a particular functional group.

In select embodiments of the present disclosure, the first cannabinoid is CBD.

In select embodiments of the present disclosure, the first cannabinoid is $\Delta^9$-THC or $\Delta^{10}$-THC.

As noted above, inducing a cannabinoid-rich solution into a supersaturated state is useful for promoting continuous cannabinoid crystallization. In select embodiments of the present disclosure, the inducing of the cannabinoid-rich solution to the supersaturated state may precede the mixing the cannabinoid-rich solution within the CSTR. Alternatively, the inducing of the cannabinoid-rich solution to the supersaturated state may be concurrent with the mixing the cannabinoid-rich solution within the CSTR.

In select embodiments of the present disclosure, the supersaturation of a cannabinoid-rich solution may be induced by controlled temperature reduction. Hence, the methods of the present disclosure may further comprise cooling the cannabinoid-rich solution, the cannabinoid-depleted solution, or a combination thereof either before or within the CSTR. For example, the cannabinoid-rich solution may comprise cannabidiol (CBD) with a CBD concentration of about 1 g/mL of solvent. In select embodiments of the present disclosure, the cannabinoid-rich solution may have a temperature of between about 0° C. and about 50° C. at an inlet to the CSTR.

In select embodiments of the present disclosure, supersaturation of a cannabinoid-rich solution may be induced by evaporation. Hence, the methods of the present disclosure may further comprise evaporating the cannabinoid-rich solution, the cannabinoid-depleted solution, or a combination thereof within the CSTR to reduce the volume of the cannabinoid-rich solution, the cannabinoid-depleted solution, or the combination thereof to between 80% and 20% of the initial volume of the cannabinoid-rich solution, the cannabinoid-depleted solution, or the combination thereof.

In select embodiments of the present disclosure, the cannabinoid-rich solution may have a viscosity of between about 0.05 cP and about 250 cP at an inlet to the CSTR. For example, the cannabinoid-rich solution may comprise CBD and have a viscosity of about 1.0 cP.

In select embodiments of the present disclosure, the cannabinoid-rich solution may have a fluid density of between about 0.2 g/mL and about 1,700 g/mL at an inlet to the CSTR. For example, the cannabinoid-rich solution may comprise CBD and have a fluid density of about 1.0 g/mL.

In select embodiments of the present disclosure, the cannabinoid-rich solution may have a temperature of between about 0° C. and about 80° C. at an inlet to the CSTR. For example, the cannabinoid-rich solution may comprise CBD and have a temperature of about 50° C.

In select embodiments of the present disclosure, the CSTR may be cylindrical in shape. The impeller may be positioned and oriented to align the axis of rotation of the impeller in a direction parallel to the cylinder axis of the CSTR. The impeller may be laterally offset from the center of the CSTR with an offset distance equal to one sixth the diameter of the CSTR. The impeller may have an impeller diameter equal to one third the diameter of the CSTR.

In select embodiments of the present disclosure, mixing the cannabinoid-rich solution under turbulent mixing conditions may include mixing the cannabinoid-rich solution with a Rushton turbine, a propeller, an anchor impeller, a gate-anchor impeller, a paddle impeller, a helical-screw impeller, a helical-ribbon impeller, or a combination thereof. For example, mixing the cannabinoid-rich solution with a propeller and/or a Rushton turbine may be advantageous when the viscosity of the cannabinoid-rich solution is below 10,000 centipoise.

As will be appreciated by those skilled in the art who have benefited from the teachings of the present disclosure, turbulent mixing conditions within a CSTR give rise to turbulent eddies with a length scale that may be quantified by the Kolmogarov length scale λ as defined as by EQN. 3 and EQN. 4.

$$\lambda = \frac{v^3}{\varepsilon^3} \quad \text{EQN. 3}$$

$$\varepsilon = P\rho D_i^3 \quad \text{EQN. 4}$$

Wherein:
ν is the fluid kinematic viscosity (in m²/s);
ε is the energy dissipation rate (kg/m·s);
P is the input power (in kg·m²/s⁻³);
ρ is the fluid density (in kg/m³); and
$D_i$ is the diameter of the CSTR impeller (in m).

In select embodiments of the present disclosure, mixing the cannabinoid-rich solution under turbulent mixing conditions may include mixing the cannabinoid-rich solution with an energy dissipation rate to produce eddies with a Kolmogorov length scale larger than the size of the crystalline cannabinoid particles. As the energy dissipation rate increases (and therefore as the input power increases) for a CSTR, the Kolmogorov length scale of eddies within the CSTR decreases. Turbulent eddies smaller than the size of the crystalline cannabinoid particles may apply shear forces to the crystalline cannabinoid particles and thereby damage the crystalline cannabinoid particles.

In select embodiments of the present disclosure, the tubular CSTR may comprise a baffle that is shaped, oriented, and positioned to redirect flow within the CSTR. For example, the baffle may be shaped, positioned, and oriented to redirect swirling flow within the CSTR to convert said swirling flow into turbulent flow. The baffle may be one of a plurality of baffles.

As noted above, the severity of the turbulent mixing conditions required to induce crystal nucleation/growth from a particular cannabinoid-rich solution will vary depending on the particulars of the cannabinoid rich solution and the extent of supersaturation. However, for any particular solution/reactor combination, there is a critical Reynolds number that defines the minimum conditions required to ensure turbulent mixing. In select embodiments of the present disclosure, the critical Reynolds number may be greater than 500, 1,000, or 10,000. As will be appreciated by those skilled in the art who have benefitted from the teachings of the present disclosure, the diameter and/or shape of the impeller and the size and shape of the reactor may impact the critical Reynolds number, and these parameters can take any of a variety of forms provided that turbulent mixing conditions are achieved within the CSTR. Likewise, the diameter and/or the capacity of the CSTR is not limited to any particular value and can vary, provided that turbulent mixing conditions are achieved within the CSTR.

In select embodiments of the present disclosure, the flow rate may be characterized as a linear flow rate, wherein the flow-rate is expressed in linear velocity units such as meters per second (m/s). Alternatively, the flow rate may be expressed as a volumetric flow rate. For example, flow rates may be expressed in volumetric velocity units such as liters per hour (L/h). Flow rates may also be expressed as a ratio of the total volume of the CSTR divided by the volumetric flow rate, for example the average residence time of fluid within the reactor (h). The flow rate may be characterized as the flow rate through an inlet to the CSTR. The flow rate may be characterized as the flow rate through an outlet to the CSTR.

In select embodiments of the present disclosure, the cannabinoid-rich solution may comprise a solvent. The solvent may comprise pentane, hexane, heptane, methanol, ethanol, isopropanol, dimethyl sulfoxide, acetone, ethyl acetate, diethyl ether, tert-butyl methyl ether, water, acetic acid, anisole, 1-butanol, 2-butanol, butane, butyl acetate, ethyl formate, formic acid, isobutyl acetate, isopropyl acetate, methyl acetate, 3-methyl-1-butanol, methylethyl ketone, 2-methyl-1-propanol, 1-pentanol, 1-propanol, propane, propyl acetate, trimethylamine, or a combination thereof.

In select embodiments, the methods of the present disclosure further comprise dispersing a plurality of seed crystals into the cannabinoid-rich solution concurrent with the mixing the cannabinoid-rich solution. In the context of the present disclosure, a seed crystal dispersion comprises at least one seed crystal dispersed in at least one solvent. A seed crystal is a crystal with a size smaller than the crystal size of the desired product. Addition of seed crystals may be advantageous as the presence of seed crystals obviates the need for nucleation during crystallization, and so long as the seed crystal size and size distribution remain constant the size and size distribution of the resulting crystalline cannabinoid particles will remain constant. Variations in the rate of nucleation contribute to variation in size distribution, therefore obviating the need for nucleation may increase the reliability of the crystallization.

Crystalline cannabinoids produced by continuous crystallization can be modified by means of salt formation, co-crystallization, derivatization (e.g. esterification, etherification, isomerization, alkylation, arylation, oxidation, reduction, ring-opening/ring-closing reactions). Previously crystallized material can be further purified by recrystallization using CSTR to obtain enhanced cannabinoid purity. Recrystallization may also be conducted on modified crystal forms (e.g. carboxylate salts, co-crystals, synthetic derivatives) originally obtained by continuous crystallization.

In select embodiments, the methods of the present disclosure further comprise flowing the plurality of crystalline cannabinoid particles and the cannabinoid-depleted solution into an additional CSTR, mixing the plurality of crystalline cannabinoid particles and the cannabinoid-depleted solution to form a plurality of larger crystalline cannabinoid particles within the additional CSTR, and discharging the plurality of larger crystalline cannabinoid particles and the cannabinoid-depleted solution from the additional CSTR in a continuous manner to provide a flow rate through the additional CSTR. Separating crystalline cannabinoid particles from the plurality of crystalline cannabinoid particles and the cannabinoid-depleted solution may include separating the larger crystalline cannabinoid particles from plurality of crystalline cannabinoid particles and the cannabinoid-depleted solution. In select embodiments, the methods of the present disclosure further comprise flowing, mixing, and discharging through a plurality of additional CSTRs in a manner substantively similar to the method described above. Operating multiple CSTRs in series, as described above, may provide near-plug flow conditions since a plurality of CSTRs possess a narrower residence time distribution than a single CSTR with a capacity equal to the total capacity of the plurality of CSTRs.

Embodiments of the present disclosure will now be described by reference to FIG. 1 to FIG. 3, which show representations of the physical structures and methods for continuously crystallizing cannabinoids according to the present disclosure.

Figure 1:
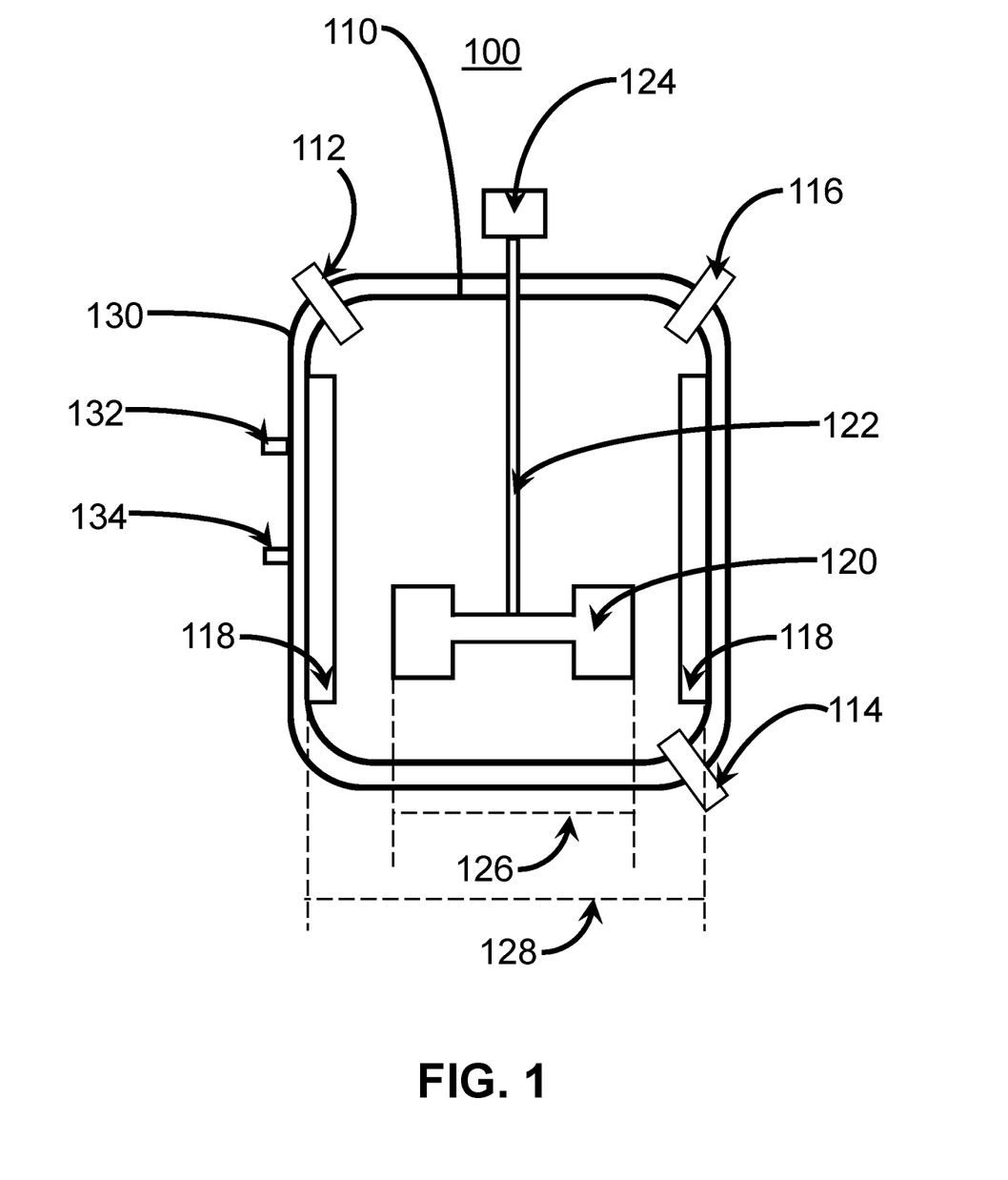
FIG. 1 shows schematic diagram of an exemplary continuous stirred-tank reactor, which may be employed in executing a method in accordance with the present disclosure.

FIG. 1 shows a schematic diagram of an exemplary CSTR 100 which may be employed in executing a method in accordance with the present disclosure. CSTR 100 comprises reaction vessel 110, inlet 112, outlet 114, additional inlet 116, a plurality of baffles 118, impeller 120, axle 122, motor 124, jacket 130, jacket inlet 132, and jacket outlet 134.

Reactor vessel 110 comprises a reactor vessel wall to define a volume within which crystallization may occur. Reactor vessel 110 may comprise impermeable and generally chemically inert materials, for example glass or stainless steel. Reactor vessel 110 possesses a cylindrical shape and a reactor vessel diameter 128. Impeller 120 is positioned and oriented to align the axis of rotation of the impeller with the cylinder axis of reactor vessel 110.

Reactor vessel 110 may be completely filled with fluid. Alternatively, reactor vessel may be partially filled with fluid, with the remaining volume filled with gas. The gas-filled volume may be referred to as head space, and the head space may be filled with inert gas, for example argon or nitrogen. The fluid within reactor vessel 110 may completely immerse impeller 120, where immersing impeller 120 may be advantageous to ensure effective mixing of the fluid within reactor vessel 110.

Impeller 120, axle 122, and motor 124 may be referred to collectively as a mixer. Impeller 120 is physically coupled to axle 122. Axle 122 is physically coupled to motor 124. Axle 122 may be physically coupled motor 124 by gears, a pulley, a transmission, or by directly coupling axle 122 to a drive shaft of motor 124. Directly physically coupling axle 122 to a drive shaft of motor 124 may include welding, bolting, and/or adhering axle 122 to a drive shaft of motor 124. Axle 122 passes through the wall of reactor vessel 110. Axle 122 may pass through the wall of reactor vessel 110 via a seal. Impeller 120 comprises a paddle impeller.

Power may be applied to motor 124, causing motor 124 to turn impeller 120 via axle 122. The rate at which motor 124 turns impeller 120 comprises a mixing speed N. Impeller 120 has an impeller diameter 126. Turning impeller 120 causes the outermost tip of impeller 120 to turn with a velocity that depends on the mixing speed N and impeller diameter 126. Fluid in contact with impeller 120 while impeller 120 turns will flow, with the nature of said flow depending on the geometry of reactor vessel 110, the mixing speed N, and impeller diameter 126. Impeller diameter 126 may advantageously be about one third of reactor vessel diameter 128 to maximize mixing efficiency.

Inlet 112 comprises a channel between reactor vessel 110 and the exterior of reactor vessel 110 through which fluids may pass. Inlet 112 comprises a tube passing through the wall of reactor vessel 110. The exterior side of inlet 112 may comprise a fitting to which a hose or a pipe may be attached. The reactor vessel side of inlet 112 may comprise a nozzle to direct the flow of fluid through inlet 112 into reactor vessel 110 in a single direction, for example downwards to fall into a layer of fluid within reactor vessel 112, or along the wall of reactor vessel 110. While inlet 112 is depicted in FIG. 1 as being located at the top of reactor vessel 110, those skilled in the art will appreciate that inlet 112 may be relocated to a variety of suitable locations in reactor vessel 110 provided that fluids are able to flow into reactor vessel 110 through inlet 112.

Outlet 114 comprises a channel between reactor vessel 110 and the exterior of reactor vessel 110 through which fluids may pass. Outlet 114 comprises a tube passing through the wall of reactor vessel 110. The exterior side of outlet 114 may comprise a fitting to which a hose or a pipe may be attached. While outlet 114 is depicted in FIG. 1 as being located at the bottom of reactor vessel 110, those skilled in the art will appreciate that outlet 114 may be relocated to a variety of suitable locations in reactor vessel 110 provided that fluids may be discharged from reactor vessel 110 through outlet 114.

In the reactor 100 depicted in FIG. 1, each of the plurality of baffles 118 is physically coupled to the interior of reactor vessel 110. Each of the plurality of baffles 118 is shaped, positioned, and oriented within reactor vessel 110 to redirect the flow of fluid within reactor vessel 110. For example, turning impeller 120 may cause fluid to adjacent to the walls of reactor vessel 110 (and therefore furthest from impeller 120) to swirl (i.e. undergo laminar flow in a direction parallel to the walls of reactor vessel 110). Plurality of baffles 118 are positioned perpendicular to the direction of said flow, causing said laminar flow to be diverted away from the wall of reactor vessel 110 and thereby cause said flow to become turbulent.

Jacket 130 surrounds reactor vessel 110. Jacket 130 forms a space around reactor vessel 110 through which a thermal fluid may be circulated. Jacket 130 comprises thermal fluid inlet 132 through which thermal fluid may enter jacket 130. Jacket 130 comprises thermal fluid outlet 134 through which thermal fluid may exit jacket 130. Thermal fluid circulating through jacket 130 may be thermally coupled to reactor vessel 110, thereby allowing heat transfer between a thermal fluid and reactor vessel 110. Reactor vessel 110 may be thermally coupled to fluids within reactor vessel 110. In other words, jacket 130 may allow heating and/or cooling of a fluid within reactor vessel 110.

Figure 2:
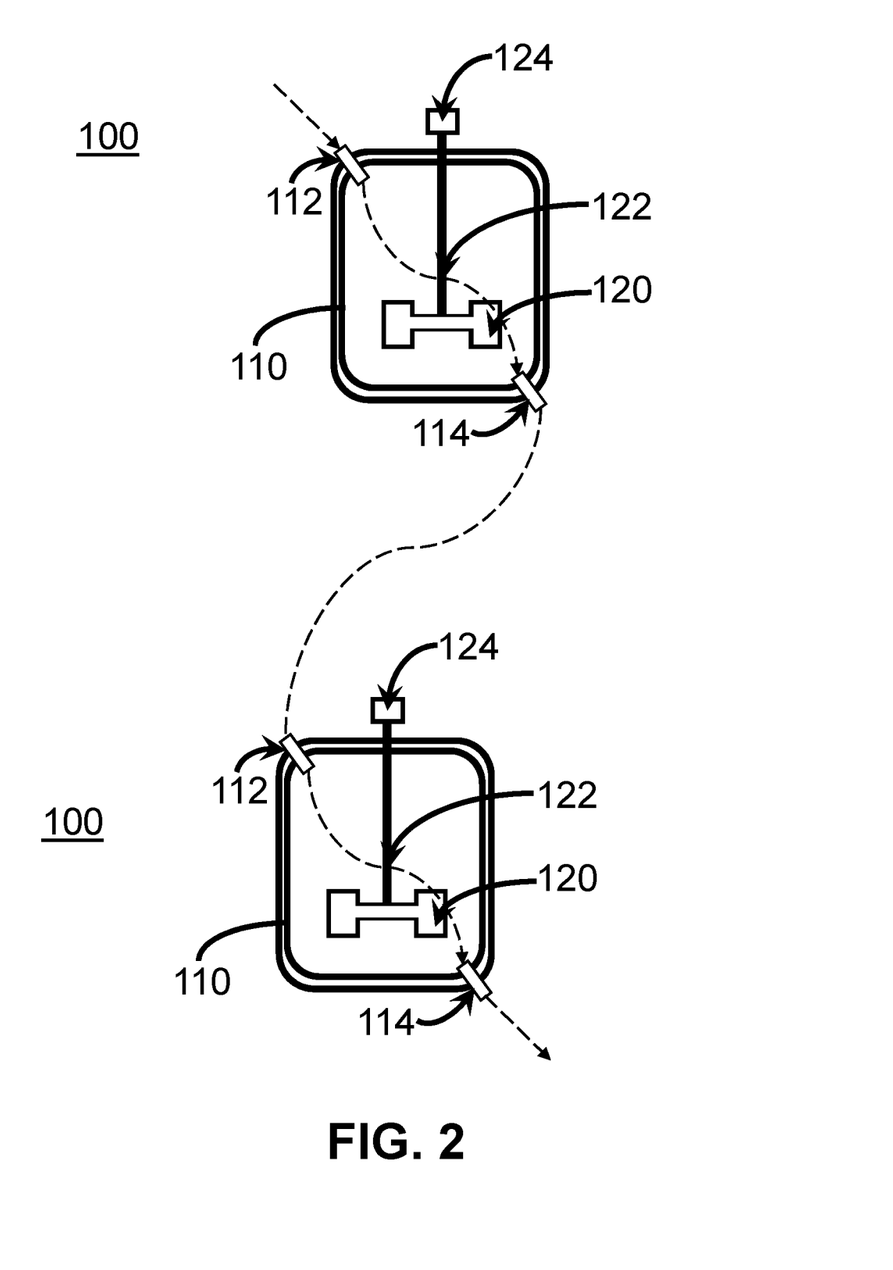
FIG. 2 shows a schematic diagram of two exemplary continuous stirred-tank reactors linked in series, which may be employed in executing a method in accordance with the present disclosure.

FIG. 2 shows a schematic diagram of two exemplary CSTRs 100 linked in series. Fluid flow in FIG. 2 is depicted by a dashed line. Fluid may enter a first CSTR 100 through a first inlet 112. Fluid may then be mixed by a first mixer comprising a first motor 124, first axle 122, and first impeller 120. Fluid may then exit first CSTR 100 via first outlet 114. Fluid may then enter a second CSTR 100 through a second inlet 112. Fluid may then be mixed by a second mixer comprising a second motor 124, second axle 122, and second impeller 120. Fluid may then exit second CSTR 100 via second outlet 114. First outlet 114 may be fluidically coupled to second inlet 112 via a pipe, a hose, a pump, or the like.

Figure 3:
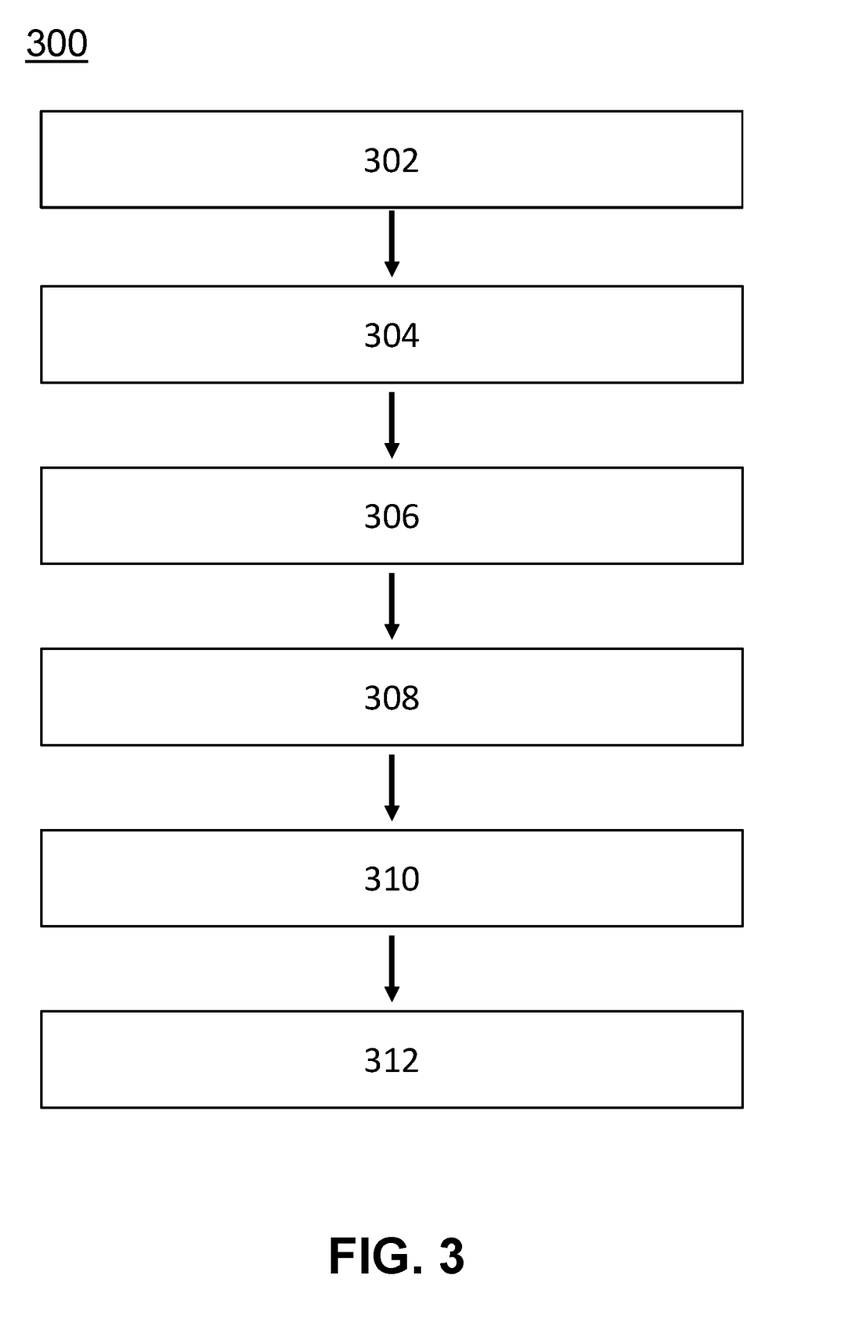
FIG. 3 shows a method for continuously preparing crystalline cannabinoid particles in accordance with the present disclosure.

FIG. 3 shows a flow diagram for a method 300 for continuously preparing crystalline cannabinoid particles. Method 300 comprises six steps: preparing a cannabinoid-rich solution that comprises a first cannabinoid (step 302); inducing the cannabinoid-rich solution to a supersaturated state in which the first cannabinoid has a supersaturated concentration that is greater than a corresponding saturation concentration of the first cannabinoid (step 304); flowing the cannabinoid-rich solution into a continuous stirred-tank reactor (CSTR) in a continuous manner (step 306); mixing the cannabinoid-rich solution under turbulent mixing conditions to form a plurality of crystalline cannabinoid particles and a cannabinoid-depleted solution within the CSTR (step 308); discharging the plurality of crystalline cannabinoid particles and the cannabinoid-depleted solution from the CSTR in a continuous manner to provide a flow rate through the CSTR (step 310); and separating crystalline cannabinoid particles from the plurality of crystalline cannabinoid particles and the cannabinoid-depleted solution in a continuous manner (step 312). In step 308, the turbulent mixing conditions are defined by a Reynolds number that is greater than a critical Reynolds number for the cannabinoid-rich solution and the CSTR. Throughout the description of method 300, equivalent physical structures from FIG. 1 and FIG. 2 are called out in brackets for illustrative purposes.

At step 302, a first cannabinoid-rich solution that comprises a first cannabinoid is prepared. The cannabinoid-rich solution may comprise a cannabinoid extract, a cannabinoid resin, a cannabinoid distillate, a cannabinoid isolate, or a combination thereof. The first cannabinoid may be $\Delta^9$-tetrahydrocannabinolic acid, $\Delta^9$-tetrahydrocannabinol, $\Delta^8$-tetrahydrocannabinolic acid, $\Delta^8$-tetrahydrocannabinol, cannabidiolic acid, cannabidiol, cannabigerolic acid, cannabigerol, cannabichromenic acid, cannabichromene, cannabinolic acid, cannabinol, $\Delta^9$-tetrahydrocannabivarinic acid, $\Delta^9$-tetrahydrocannabivarin, cannabigerivarin, cannabidivarin, cannabichromevarin, 11-hydroxy-$\Delta^9$-tetrahydrocannabinol, 11-nor-9-carboxy-$\Delta^9$-tetrahydrocannabinol, or a combination thereof. The cannabinoid-rich solution may comprise $\Delta^9$-tetrahydrocannabinolic acid, $\Delta^9$-tetrahydrocannabinol, $\Delta^8$-tetrahydrocannabinolic acid, $\Delta^8$-tetrahydrocannabinol, cannabidiolic acid, cannabidiol, cannabigerolic acid, cannabigerol, cannabichromenic acid, cannabichromene, cannabinolic acid, cannabinol, $\Delta^9$-tetrahydrocannabivarinic acid, $\Delta^9$-tetrahydrocannabivarin, cannabigerivarin, cannabidivarin, cannabichromevarin, 11-hydroxy-$\Delta^9$-tetrahydrocannabinol, 11-nor-9-carboxy-$\Delta^9$-tetrahydrocannabinol, or a combination thereof.

The cannabinoid-rich solution may comprise a solvent. The solvent may comprise pentane, hexane, heptane, methanol, ethanol, isopropanol, dimethyl sulfoxide, acetone, ethyl acetate, diethyl ether, tert-butyl methyl ether, water, acetic acid, anisole, 1-butanol, 2-butanol, butane, butyl acetate, ethyl formate, formic acid, isobutyl acetate, isopropyl acetate, methyl acetate, 3-methyl-1-butanol, methylethyl ketone, 2-methyl-1-propanol, 1-pentanol, 1-propanol, propane, propyl acetate, trimethylamine, or a combination thereof. The cannabinoid-rich solution may further comprise an excipient. In the context of method 300, the cannabinoid-rich solution may comprise a solvent, or a mixture of solvents. A mixture of solvents may be advantageous to achieve a desired nucleation or crystal growth rate. The solvent may comprise a Class III solvent, where Class III solvents are advantageous for active pharmaceutical ingredient preparation due to their low toxicity.

At step 304, the cannabinoid-rich solution is induced to a supersaturated state. As discussed above, a solvent is supersaturated when the concentration of solute in a given solution is above the solubility limit for said solution. The degree of supersaturation of a solution comprises the amount by which the concentration of the supersaturated solution exceeds the saturation concentration of said supersaturated solution. The degree of supersaturation may be expressed in absolute units (e.g. moles/liter or grams/liter) or in relative units (e.g. [solute concentration]/[saturation concentration]×100%). Supersaturating a cannabinoid solution may include causing a solution to possess a solute concentration above the solubility limit of the solvent. A person of ordinary skill in the art will appreciate that the solubility limit of a given cannabinoid solution depends on at least the temperature of the solution, the cannabinoid in question, the solvent in question, and the presence of any non-solvents. Non-exclusive methods by which a solution may be supersaturated include cooling, evaporation, and adding a non-solvent.

The saturation concentration of a cannabinoid in a solvent depends on the temperature of the solution, with a higher temperature typically yielding a higher saturation concentration. A saturated solution may be prepared by combining an excess amount a solid (i.e. undissolved) cannabinoid with a solvent at a temperature equal to the boiling point of the solid. A portion of the cannabinoid will dissolve in the solvent, with the excess being unable to dissolve due to saturation of the solvent with dissolved cannabinoid. The undissolved solid cannabinoid may then be separated from the cannabinoid solution to yield a saturated cannabinoid solution. Cooling of said saturated solution will decrease the solubility limit of the solvent, and since the amount of cannabinoid dissolved in the solution is now above the new solubility limit the solution becomes supersaturated by cooling.

The saturation concentration of a cannabinoid in a solvent depends on the composition of the solvent. The solvent may comprise a mixture of solvents, where the mixture of solvents may comprise at least one cannabinoid solvent and at least one cannabinoid non-solvent. A cannabinoid solvent is a solvent that is able to dissolve at least twice the amount of the cannabinoid as the cannabinoid non-solvent. The cannabinoid may be dissolved in the cannabinoid solvent to saturate the cannabinoid solvent, then the cannabinoid solution may be mixed with the cannabinoid non-solvent to form the mixture of solvents. The presence of the non-solvent decreases the saturation concentration of the cannabinoid in the mixture of solvents. The mixture of solvents may therefore become supersaturated by decreasing the saturation concentration of the cannabinoid in the mixture of solvents below the actual concentration of the cannabinoid in the mixture.

At step 306, the cannabinoid-rich solution is flowed into a CSTR (100) in a continuous manner. The CSTR (100) may comprise a reaction vessel (110), an inlet (112) comprising an opening in the reaction vessel (110) through which the first cannabinoid solution flows, an outlet (114), an additional inlet (116), a baffle (118), a mixer comprising an impeller (120), an axle (122), and a motor (124), and a jacket (130) comprising a jacket inlet (132), and jacket outlet (134). The baffle (118) may be shaped, oriented, and/or positioned to redirect flow within the CSTR. The baffle (118) may be one of a plurality of baffles (118). The CSTR (100) may be cylindrical, and the impeller (120) may be positioned and oriented to align the axis of rotation of the impeller with the cylinder axis.

The cannabinoid-rich solution may have a viscosity of between about 0.05 and about 250 cP at an inlet (112) to the CSTR. The cannabinoid-rich solution may have a fluid density of between about 0.02 g/mL and about 1,700 g/mL at an inlet (112) to the CSTR. The cannabinoid-rich solution may have a temperature of between about 0° C. and about 80° C. at an inlet (112) to the CSTR.

At step 308, the cannabinoid-rich solution is mixed under turbulent mixing conditions to form a plurality of crystalline cannabinoid particles and a cannabinoid-depleted solution within the CSTR (100). The cannabinoid-rich solution may mixed under turbulent mixing conditions with a mixer comprising an impeller (120), an axle (122), and a motor (124). The critical Reynolds number may be about equal to a Reynolds number above which a power number for the reactor is about constant. The critical Reynolds number may be greater than 10,000. Mixing the cannabinoid-rich solution under turbulent mixing conditions may include mixing the cannabinoid-rich solution with an impeller (120), the impeller comprising a Rushton turbine, a propeller, an anchor impeller, a gate-anchor impeller, a paddle impeller, a helical screw impeller, a helical ribbon impeller, or any combination thereof. Mixing the cannabinoid-rich solution with the mixer may include turbulently mixing the cannabinoid-rich solution with the mixer wherein the impeller diameter (126) is about one third the diameter of the CSTR (128).

Mixing the cannabinoid-rich solution under turbulent mixing conditions may include mixing the cannabinoid-rich solution with an energy dissipation rate to produce eddies with a Kolmogorov length scale larger than the size of the crystalline cannabinoid particles.

Crystallization may occur in a supersaturated solution via homogeneous nucleation. In homogeneous nucleation, dissolved individual solute molecules may encounter other dissolved individual solute molecules in a supersaturated solution and agglomerate together to form a small crystal nucleus. The crystal nucleus may then grow larger as additional solute molecules encounter and thereby attach to the surface of the crystal nucleus. However, while the interior bulk of a growing crystal is thermodynamically stable, the surface of the crystal is typically unstable, and thermodynamic instability provides an energy barrier to growth. For large crystal nuclei, the surface area to volume ratio is small which negates the energy barrier and causes crystal growth to be thermodynamically favorable, making large crystal nuclei stable. The rate of nucleation is the rate at which stable crystal nuclei form. A stable crystal nucleus may grow effectively indefinitely to form a large crystal. Small crystal nuclei have a high surface area to volume ratio which causes the energy barrier to growth to become significant, which makes dissolution of the small crystal nuclei thermodynamically favorable and causes small nuclei to be unstable. However, while dissolution of the small nuclei is favored, there exists a non-zero statistical probability that a small nucleus will grow to large enough to become stable and eventually grow to become a large crystal. The probability of an unstable crystal nucleus growing large enough to become stable, and thereby the rate of formation of stable crystal nuclei, increases as the degree of supersaturation of the solution increases. In other words, a higher degree of supersaturation of the solution increases the rate of homogeneous nucleation. Depending on the degree of supersaturation, the amount of time required to form at least one stable crystal nucleus may be on the order of second, hours, days, or months.

Crystallization may occur in a supersaturated solution via heterogeneous nucleation. In heterogeneous nucleation, seed crystals are added to the supersaturated solution. Dissolved individual solute molecules may encounter and thereby attach to the surface of the seed crystal, causing the seed crystal to grow and eventually form a large crystal. A seed crystal may comprise the same material as the solute, or a different material from the solute. For example, seed crystals may be produced by milling the crystalline product of a previous crystallization to produce a large number of small seed crystals composed of the same material as the product to be crystallized. The presence of seed crystals in the supersaturated solution allows crystal growth to occur without the need for homogeneous nucleation. Homogeneous nucleation may require a relatively high degree of supersaturation.

Inducing of the cannabinoid-rich solution to the supersaturated state may precedes the mixing the cannabinoid-rich solution. Inducing of the cannabinoid-rich solution to the supersaturated state may be concurrent with the mixing the cannabinoid-rich solution. In the context of the present disclosure, a narrow size distribution may be advantageous since a continuous separation method may be optimised to separate particles of a certain size and a narrow size distribution ensures the maximum number are of the optimal size. Crystalline cannabinoid particles with a size that closely matches the expected size will therefore also be closest to the optimal size of the separation method.

At step 310, the plurality of crystalline cannabinoid particles and the cannabinoid-depleted solution are discharged from the CSTR (100) in a continuous manner to provide a flow rate through the CSTR. The plurality of crystalline cannabinoid particles and the cannabinoid-depleted solution may be discharged via an outlet (114).

At step 312, the crystalline cannabinoid particles are separated from the plurality of crystalline cannabinoid particles and the cannabinoid-depleted solution in a continuous manner. Continuous separation may include centripetal separation, filter separation, and settling. As mentioned above, continuously separating crystalline cannabinoid particles is more efficient when the size and size distribution of the crystalline cannabinoid particles closely matches the size for which the separation method has been optimised. Separating the crystalline cannabinoid particles from the cannabinoid-depleted solution may include forming a mother liquor.

The method 300 may further comprise reducing the volume of the mother liquor to form a concentrated mother liquor and a recycled solvent. The method 300 may further comprise mixing the concentrated mother liquor with a second cannabinoid solution to form a follow-on quantity of cannabinoid-rich solution. The follow-on quantity of cannabinoid-rich solution may comprise at least a portion of the first cannabinoid. Mixing the concentrated mother liquor with the second cannabinoid solution to form the follow-on quantity of cannabinoid-rich solution may increase the efficiency of the crystallization, since a portion of the dissolved cannabinoid that was not initially crystallized may crystallize when the concentrated mother liquor passes through the CSTR (100).

The method 300 may further comprise dissolving at least a portion of the cannabinoid in the recycled solvent to form a third cannabinoid solution, dissolving the remainder of the cannabinoid in the solvent to form a fourth cannabinoid solution, and mixing the third and fourth cannabinoid solution to form the first cannabinoid solution. Using the recycled solvent to form the first cannabinoid solution decreases the cost of the crystallization since some of the solvent used for the crystallization may be re-used.

The method 300 may further comprise cooling the cannabinoid-rich solution, the cannabinoid-depleted solution, or a combination thereof within the CSTR. The cannabinoid-rich solution, the cannabinoid-depleted solution, or a combination thereof within the CSTR may be cooled by flowing a thermal fluid into a jacket (130) through a jacket inlet (132) and a jacket outlet (134).

The method 300 may further comprise dispersing a plurality of seed crystals into the cannabinoid-rich solution concurrent with the mixing the cannabinoid-rich solution. The plurality of seed crystals may be dispersed into the cannabinoid-rich solution by flowing a dispersion comprising the plurality of seed crystals through an additional inlet (116). The plurality of seed crystals may be dispersed into the cannabinoid-rich solution by mixing a dispersion comprising the plurality of seed crystals with the cannabinoid-rich solution.

The method 300 may further comprise evaporating the cannabinoid-rich solution, the cannabinoid-depleted solution, or a combination thereof within the CSTR to reduce the volume of the cannabinoid-rich solution, the cannabinoid-depleted solution, or the combination thereof to between 80% and 20% of the initial volume of the cannabinoid-rich solution, the cannabinoid-depleted solution, or the combination thereof. Evaporating the cannabinoid-rich solution, the cannabinoid-depleted solution, or a combination thereof may include evaporating the cannabinoid-rich solution, the cannabinoid-depleted solution, or a combination thereof under reduced pressure.

The method 300 may further comprise flowing the plurality of crystalline cannabinoid particles and the cannabinoid-depleted solution into an additional CSTR (100), mixing the plurality of crystalline cannabinoid particles and the cannabinoid-depleted solution to form a plurality of larger crystalline cannabinoid particles within the additional CSTR (100), and discharging the plurality of larger crystalline cannabinoid particles and the cannabinoid-depleted solution from the additional CSTR (100) in a continuous manner to provide a flow rate through the additional CSTR (100). Separating crystalline cannabinoid particles from the plurality of crystalline cannabinoid particles and the cannabinoid-depleted solution may include separating the larger crystalline cannabinoid particles from plurality of crystalline cannabinoid particles and the cannabinoid-depleted solution.

In the present disclosure, all terms referred to in singular form are meant to encompass plural forms of the same. Likewise, all terms referred to in plural form are meant to encompass singular forms of the same. Unless defined otherwise, all technical and scientific terms used herein have the same meaning as commonly understood by one of ordinary skill in the art to which this disclosure pertains.

As used herein, the term "about" refers to an approximately +/−10% variation from a given value. It is to be understood that such a variation is always included in any given value provided herein, whether or not it is specifically referred to.

It should be understood that the compositions and methods are described in terms of "comprising," "containing," or "including" various components or steps, the compositions and methods can also "consist essentially of or "consist of the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Although individual embodiments are discussed, the disclosure covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

Many obvious variations of the embodiments set out herein will suggest themselves to those skilled in the art in light of the present disclosure. Such obvious variations are within the full intended scope of the appended claims.

The invention claimed is:

1. A method for producing crystalline cannabinoid particles in continuous mode, the method comprising:
    preparing a cannabinoid-rich solution that comprises a first cannabinoid;
    inducing the cannabinoid-rich solution to a supersaturated state in which the first cannabinoid has a supersaturated concentration that is greater than a corresponding saturation concentration of the first cannabinoid;
    flowing the cannabinoid-rich solution into a continuous stirred-tank reactor, CSTR, in a continuous manner;
    mixing the cannabinoid-rich solution under turbulent mixing conditions to form a plurality of crystalline cannabinoid particles and a cannabinoid-depleted solution within the CSTR;
    discharging the plurality of crystalline cannabinoid particles and the cannabinoid-depleted solution from the CSTR in a continuous manner to provide a flow rate through the CSTR; and
    separating crystalline cannabinoid particles from the plurality of crystalline cannabinoid particles and the cannabinoid-depleted solution in a continuous manner,
    wherein the turbulent mixing conditions are defined by a Reynolds number that is greater than a critical Reynolds number for the cannabinoid-rich solution and the CSTR.

2. The method of claim 1, wherein the critical Reynolds is about equal to a Reynolds number above which a power number for the reactor is about constant.

3. The method of claim 1, wherein the CSTR comprises a baffle that is shaped, oriented, or positioned to redirect flow within the CSTR.

4. The method of claim 3, wherein the baffle is one of a plurality of baffles.

5. The method of claim 1, further comprising cooling the cannabinoid-rich solution, the cannabinoid-depleted solution, or a combination thereof within the CSTR.

6. The method of claim 1, wherein the first cannabinoid is THC ($\Delta$9-THC), THCA, $\Delta$8-THC, trans-$\Delta$10-THC, cis $\Delta$10-THC, THCV, THCVA, $\Delta$8-THCV, $\Delta$9-THCV, CBD, CBDA, CBDV, CBDVA, CBC, CBCA, CBCV, CBCVA, CBG, CBGA, CBGV, CBGVA, CBN, CBNA, CBNV, CBNVA, CBND, CBNDA, CBNDV, CBNDVA, CBE, CBEA, CBEV, CBEVA CBL, CBLA, CBLV, CBLVA, CBT, CBTA, or cannabicitran.

7. The method of claim 1, wherein the cannabinoid-rich solution comprises a cannabinoid extract, a cannabinoid resin, a cannabinoid distillate, a cannabinoid isolate, or a combination thereof.

8. The method of claim 1, wherein the cannabinoid-rich solution comprises THC ($\Delta$9-THC), THCA, $\Delta$8-THC, trans-$\Delta$10-THC, cis $\Delta$10-THC, THCV, THCVA, $\Delta$8-THCV, $\Delta$9-THCV, CBD, CBDA, CBDV, CBDVA, CBC, CBCA, CBCV, CBCVA, CBG, CBGA, CBGV, CBGVA, CBN, CBNA, CBNV, CBNVA, CBND, CBNDA, CBNDV, CBNDVA, CBE, CBEA, CBEV, CBEVA CBL, CBLA, CBLV, CBLVA, CBT, CBTA, cannabicitran, or a combination thereof.

9. The method of claim 1, wherein the cannabinoid-rich solution comprises a solvent, and wherein the solvent comprises pentane, hexane, heptane, methanol, ethanol, isopropanol, dimethyl sulfoxide, acetone, ethyl acetate, diethyl ether, tert-butyl methyl ether, water, acetic acid, anisole, 1-butanol, 2-butanol, butane, butyl acetate, ethyl formate, formic acid, isobutyl acetate, isopropyl acetate, methyl acetate, 3-methyl-1-butanol, methyl ethyl ketone, 2-methyl-1-propanol, 1-pentanol, 1-propanol, propane, propyl acetate, trimethylamine, or a combination thereof.

10. The method of claim 1, wherein the cannabinoid-rich solution has a viscosity of between about 0.05 cP and about 250 cP at an inlet to the CSTR.

11. The method of claim 1, wherein the cannabinoid-rich solution has a fluid density of between about 0.2 g/mL and about 1,700 g/mL at an inlet to the CSTR.

12. The method of claim 1, wherein the cannabinoid-rich solution has a temperature of between about 0° C. and about 80° C. at an inlet to the CSTR.

13. The method of claim 1, wherein the inducing of the cannabinoid-rich solution to the supersaturated state precedes the mixing of the cannabinoid-rich solution.

14. The method of claim 1, wherein the inducing of the cannabinoid-rich solution to the supersaturated state is concurrent with the mixing the cannabinoid-rich solution.

15. The method of claim 1, wherein the cannabinoid-rich solution further comprises an excipient.

16. The method of claim 1, further comprising dispersing a plurality of seed crystals into the cannabinoid-rich solution concurrent with the mixing the cannabinoid-rich solution.

17. The method of claim 1, further comprising:
flowing the plurality of crystalline cannabinoid particles and the cannabinoid-depleted solution into an additional CSTR;
mixing the plurality of crystalline cannabinoid particles and the cannabinoid-depleted solution to form a plurality of larger crystalline cannabinoid particles within the additional CSTR; and
discharging the plurality of larger crystalline cannabinoid particles and the cannabinoid-depleted solution from the additional CSTR in a continuous manner to provide a flow rate through the additional CSTR,
wherein separating crystalline cannabinoid particles from the plurality of crystalline cannabinoid particles and the cannabinoid-depleted solution comprises separating the larger crystalline cannabinoid particles from plurality of crystalline cannabinoid particles and the cannabinoid-depleted solution.

18. The method of claim 1, wherein the mixing of the cannabinoid-rich solution under the turbulent mixing conditions comprises mixing the cannabinoid-rich solution with an energy dissipation rate that is sufficient to produce eddies with a Kolmogorov length scale that is larger than the size of the crystalline cannabinoid particles.

19. The method of claim 1, further comprising evaporating the cannabinoid-rich solution, the cannabinoid-depleted solution, or a combination thereof within the CSTR to reduce the volume of the cannabinoid-rich solution, the cannabinoid-depleted solution, or the combination thereof to between 80% and 20% of the initial volume of the cannabinoid-rich solution, the cannabinoid-depleted solution, or the combination thereof.

* * * * *